United States Patent [19]

Fahrenkrug et al.

[11] Patent Number: 5,411,498
[45] Date of Patent: May 2, 1995

[54] STRETCHABLE SHAPED ABSORBENT GARMENT

[75] Inventors: Anne M. Fahrenkrug, Oshkosh; Neal A. Rollins, Menasha; Marion C. Morris, Appleton; John A. Rooyakkers, Little Chute; Cathy L. Winters, Appleton, all of Wis.

[73] Assignee: Kimberly-Clark Corporation, Neenah, Wis.

[21] Appl. No.: 268,042

[22] Filed: Jun. 29, 1994

Related U.S. Application Data

[63] Continuation of Ser. No. 833,561, Feb. 5, 1992, abandoned, which is a continuation of Ser. No. 504,158, Apr. 2, 1990, abandoned.

[51] Int. Cl.6 .................. A61F 13/64; A61F 13/15
[52] U.S. Cl. .................. 604/385.2; 604/385.1; 604/392
[58] Field of Search .............. 604/385.2, 400, 402, 604/385.1, 392

[56] References Cited

U.S. PATENT DOCUMENTS

| | | | |
|---|---|---|---|
| D. 266,024 | 8/1982 | Ternstrom et al. | D24/50 |
| D. 276,846 | 12/1984 | Widlund et al. | D24/51 |
| D. 301,061 | 5/1989 | Ternstrom et al. | D24/50 |
| D. 301,375 | 5/1989 | Ternstrom et al. | D24/50 |
| 813,221 | 2/1906 | Longstreth | |
| 1,788,756 | 1/1931 | White | |
| 1,793,243 | 2/1931 | Peterson et al. | |
| 1,905,964 | 4/1933 | Hammond | |
| 2,273,542 | 2/1942 | Tasker | |
| 2,333,839 | 11/1943 | Blackburn et al. | 128/290 |
| 2,866,459 | 12/1958 | Sobelson | |
| 2,871,859 | 2/1959 | Dunn | 604/402 |
| 2,964,040 | 12/1960 | Ashton et al. | 128/290 |
| 2,964,041 | 12/1960 | Ashton et al. | 128/290 |
| 3,014,482 | 12/1961 | Case | 128/291 |
| 3,236,238 | 2/1966 | Morse | 128/290 |
| 3,245,406 | 4/1966 | Chardack | 128/156 |
| 3,262,451 | 7/1966 | Morse | 128/290 |
| 3,357,425 | 12/1967 | Morgan | 128/156 |
| 3,371,668 | 3/1968 | Johnson | 128/290 |
| 3,460,536 | 8/1969 | Champaigne, Jr. | 128/290 |
| 3,468,748 | 9/1969 | Bassett | 161/122 |
| 3,575,174 | 4/1971 | Mogor | 128/290 |
| 3,599,640 | 8/1971 | Larson | 128/286 |
| 3,779,246 | 12/1973 | Mesek et al. | 128/287 |
| 3,856,012 | 12/1974 | MacDonald et al. | 128/284 |
| 4,050,462 | 9/1977 | Woon et al. | 604/385.2 X |
| 4,166,464 | 9/1979 | Korpman | 128/287 |
| 4,231,358 | 11/1980 | Atchison | 128/168 |
| B1 4,315,508 | 11/1988 | Bolick | 604/392 |
| 4,319,572 | 3/1982 | Widlund et al. | 128/284 |
| 4,323,070 | 4/1982 | Ternstrom et al. | 128/287 |
| 4,355,425 | 10/1982 | Jones et al. | 2/402 |
| 4,397,645 | 8/1983 | Buell | 604/380 |
| 4,430,088 | 2/1984 | Karami | 604/385.1 |
| 4,450,414 | 9/1985 | Wishman | 604/378 |
| 4,496,359 | 1/1985 | Pignuel | 604/387 |
| 4,502,156 | 3/1985 | Wishman | 2/181 |
| 4,525,407 | 6/1985 | Ness | 428/138 |
| 4,527,989 | 7/1985 | Karami | 604/385 A |

(List continued on next page.)

FOREIGN PATENT DOCUMENTS

| | | |
|---|---|---|
| 0167931A2 | 1/1986 | European Pat. Off. |
| 0228353 | 7/1987 | European Pat. Off. |
| 0235815A3 | 9/1987 | European Pat. Off. |
| 0287388 | 10/1988 | European Pat. Off. |
| 3423644 | 1/1986 | Germany ............ 604/385.2 |
| 83/7490 | 10/1983 | South Africa . |
| 888827 | 2/1962 | United Kingdom . |
| 2182840 | 5/1987 | United Kingdom . |
| WO88/05269 | 7/1988 | WIPO . |

*Primary Examiner*—David H. Willse
*Attorney, Agent, or Firm*—Thomas M. Gage; Thomas J. Mielke

[57] ABSTRACT

A stretchable absorbent garment having a fluid-pervious inner layer, an outer layer, and an absorbent structure located between said inner and outer layers, and at least two generally parallel elastomeric strands stretch bonded to the garment along its length such that when in a relaxed state, all of the above described elements are reduced in length.

24 Claims, 8 Drawing Sheets

U.S. PATENT DOCUMENTS

| | | | |
|---|---|---|---|
| 4,534,769 | 8/1985 | De Jonhkeere et al. | 604/369 |
| 4,552,795 | 11/1985 | Hansen et al. | 428/110 |
| 4,579,556 | 4/1986 | McFarland | 604/385 A |
| 4,589,878 | 5/1986 | Mitrani | 604/392 |
| 4,606,964 | 8/1986 | Wideman | 428/152 |
| 4,626,305 | 12/1986 | Suzuki et al. | 156/164 |
| 4,639,949 | 2/1987 | Ales et al. | 2/400 |
| 4,640,859 | 2/1987 | Hansen et al. | 428/105 |
| 4,642,819 | 2/1987 | Ales et al. | 2/400 |
| 4,666,542 | 5/1987 | De Jonckheere | 156/164 |
| 4,668,230 | 5/1987 | Damico et al. | 604/385 |
| 4,670,012 | 6/1987 | Johnson | 604/390 |
| 4,687,477 | 8/1987 | Suzuki et al. | 604/385 A |
| 4,692,163 | 9/1987 | Widlund et al. | 604/385 A |
| 4,699,620 | 10/1987 | Bernardin | 604/385 A |
| 4,701,177 | 10/1987 | Ellis et al. | 604/385 |
| 4,704,116 | 11/1987 | Enloe | 604/385 A |
| 4,726,807 | 2/1988 | Young et al. | 604/385 A |
| 4,731,066 | 3/1988 | Korpman | 604/366 |
| 4,731,070 | 3/1988 | Koci | 604/385 R |
| 4,743,241 | 5/1988 | Igaue et al. | 604/385 A |
| 4,758,241 | 7/1988 | Papajohn | 604/387 |
| 4,762,582 | 8/1988 | de Jonckheere | 156/164 |
| 4,770,657 | 9/1988 | Ellis et al. | 604/385 A |
| 4,771,483 | 9/1988 | Hooreman et al. | 2/237 |
| 4,776,911 | 11/1988 | Uda et al. | 156/161 |
| 4,795,451 | 1/1989 | Buckley | 604/385.2 |
| 4,795,452 | 1/1989 | Blaney et al. | 604/385.1 |
| 4,798,603 | 1/1989 | Meyer et al. | 604/378 |
| 4,808,177 | 2/1989 | Des Marais et al. | 604/385.1 |
| 4,808,178 | 2/1989 | Aziz et al. | 604/385.2 |
| 4,816,026 | 3/1989 | Richardson | 604/385.2 |
| 4,847,134 | 7/1989 | Fahrenkrug et al. | 428/138 |
| 4,895,568 | 1/1990 | Enloe | 604/385.2 |
| 4,911,701 | 3/1990 | Mauinkurve | 604/385.2 |
| 4,935,021 | 6/1990 | Huffman et al. | 604/385.2 X |
| 4,935,287 | 6/1990 | Johnson et al. | 428/198 |

STRETCHABLE SHAPED ABSORBENT GARMENT

This is a continuation of application Ser. No. 07/833,561, filed on Feb. 5, 1992, now abandoned which is a continuation of Ser. No. 07/504,158, filed on Apr. 2, 1990, now abandoned.

BACKGROUND OF THE INVENTION

1. Field of the Invention

The present invention relates to an absorbent garment suitable for use in absorbing body fluids. Specifically, the present invention relates to a stretchable shaped absorbent garment.

2. Description of the Related Art

It has been recognized that introducing a degree of stretchability into personal care products such as diapers, sanitary napkins, adult incontinent products and the like can provide said products with certain benefits. For example, U.S. Pat. No. 2,866,459 issued Dec. 30, 1958 to Sobelson describes a stretchable, reusable cotton diaper. Stretchability is imparted to the cotton fabric by the presence of longitudinal and transverse elastic stitching. The stitching is described as imparting longitudinal curvature and transverse curvature to the diaper. This curvature is described as producing a diaper formed permanently in the shape required for use.

U.S. Pat. No. 3,371,668, issued Mar. 5, 1968 to Johnson, is directed to a sanitary napkin employing a nonwoven fabric with machine direction elasticity as a cover. The described fabric comprises a nonwoven web of fibers having a plurality of elastic means, in extended condition, secured to the web. Upon their release, the fabric contracts in the length direction and is characterized by a plurality of substantially parallel buckled areas having improved bulk.

U.S. Pat. No. 4,606,964 issued Aug. 19, 1986 to Wideman is directed to a bulked web composite and method of making the same. Described is a composite formed by adhering a reticulated web of elastic material to at least one gatherable web whereby, upon release of the tensioning forces, the gatherable web is gathered by the reticulated web to form a bulked web composite. It is generally described that the reticulated web of the elastic material is elongated by differentially tensioning it, thus forming a composite having greater bulk corresponding to those areas of the reticulated web which are placed under a greater tensioning force.

U.S. Pat. No. 4,847,134 issued Jul. 11, 1989 to Fahrenkrug, et al. is directed to a stretchable absorbent undergarment. Described is a stretchable undergarment comprising a body-side layer, a liquid impervious outer layer, an absorbent layer and a stretchable layer. The stretchable layer comprises a continuous layer of stretchable material which may be perforated. The perforations render the elastomeric layer permeable. The elastomeric layer can be stretch bonded to the other layers such that upon relaxation the stretchable layer forms a plurality of rugosities in the body-side layer, outer layer and absorbent medium.

From the above, it can be seen that in the past, when stretchable materials were employed in absorbent products, they often imparted stretchability to only one component (e.g., the cover) of the absorbent product. While certain advantages can be brought to the absorbent products through the use of such stretchable materials, the use of such materials as only a single component of the product prevented such products from achieving certain other advantages. Moreover, even when stretchability was imparted to an entire absorbent product, such as in U.S. Pat. No. 4,847,134, such products are not believed to have been developed to their greatest extent. For example, in U.S. Pat. No. 4,847,134, the use of the stretchable web may, in some instances, adversely affect the absorption of body fluids depending on the placement of the stretchable layer within the absorbent product and its ability to pass a fluid.

SUMMARY OF THE INVENTION

It is desirable to provide a stretchable absorbent garment for absorbing body liquids. It is further desired that the absorbent product be easily manufactured and that the inducement of stretchability not unacceptably deleteriously affect the absorbent capability of the garment.

Further, it is desirable to produce a stretchable absorbent garment which is capable of being shaped to conform to the body of a user. Moreover, it is desirable to provide stretchable attachment means integrally attached to the garment which attachment means are capable of holding the garment in place during use. It is further desired that the stretchable garment be generally soft to the touch, comfortable to wear during use, breathable, have soft body-contact surfaces and provide an acceptable degree of absorption capability without being unduly bulky or noticeable when worn under clothing. It is to these goals that the present invention is directed.

The present invention is directed to a stretchable absorbent garment. The garment includes a fluid-pervious inner layer, an outer layer, an absorbent structure sandwiched between said inner and outer layers, and at least two generally parallel elastomeric strands stretch bonded to the garment along its length such that, when in a relaxed state, the elastomeric strands reduce the length of the inner layer, outer layer and absorbent structure across the width of the garment. Because the garment, including the absorbent structure, is stretchable, the garment is self adjusting in fit and is generally capable of concentrating the absorbent structure in the needed area to the greatest extent possible.

In another aspect, the present invention concerns a stretchable, shaped absorbent garment having stretchable attachment means attached integrally thereto. Because the attachment means are stretchable, they are capable of infinite adjustment on users of different shapes and sizes to provide the best fit possible. In another aspect, the present invention is directed to a stretchable absorbent garment which is capable of being shaped both along its length and width by selectively placing the stretchability imparting elastomeric strands in different locations along the width and throughout the thickness of the garment, all of the elastomeric strands extending along at least a portion of the length of the garment.

DETAILED DESCRIPTION OF THE PREFERRED EMBODIMENT

The present invention is directed to a stretchable absorbent garment. The entire garment is capable of being stretched and, in a relaxed state, contracts to form a garment having a reduced length with a plurality of rugosities extending generally across the width of the garment. The garment has a length, a width, and a thickness and comprises (a) a fluid-pervious inner layer having a length and a width; (b) an outer layer having a length and a width; (c) an absorbent structure having a length and a width, said absorbent structure being located between said inner and outer layers; and (d) at least two generally parallel elastomeric strands stretch bonded to the garment along substantially its entire length such that, when in a relaxed state, said elastomeric strands reduce the length of said inner layer, outer layer and absorbent structure across the width of the garment.

Figure 1:
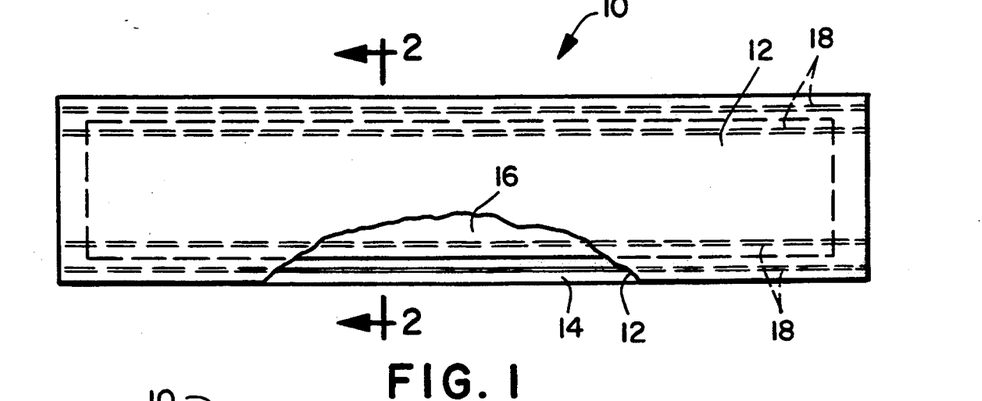
FIG. 1 is a top plan view of one embodiment of a stretchable absorbent garment according to the present invention in a stretched state.

The invention can best be understood by reference to the drawings wherein FIG. 1 illustrates a top plan view of one embodiment of a garment 10 according to the present invention in a stretched state. The garment 10 comprises a fluid-pervious inner layer 12, an outer layer 14, and an absorbent structure 16 located between the inner layer 12 and outer layer 14. The inner layer 12 is generally adapted to contact the skin of a wearer. Accordingly, the inner layer 12 is generally fluid-pervious and capable of passing body liquids at a rate generally sufficient to prevent leakage from the garment when in use. The absorbent structure 16 is capable of absorbing a body liquid such as urine or other body discharges. The outer layer 14 may be a generally soft, almost clothlike material to provide a pleasant feel to the product or, may be in the form of a fluid-impervious material to prevent passage of body liquids externally of the garment 10.

Elastomeric strands 18 extend along the length of the garment in a generally parallel relationship to one another. At least two and desirably at least four elastomeric strands are present in the garments according to the present invention. Preferably, a plurality of elastomeric strands are present in the garments and are spaced generally across the entire width of the garment. The elastomeric strands are stretch bonded to the garment such that, in a relaxed state, the elastomeric strands contract and thus reduce the length of the inner layer 12, outer layer 14, and absorbent structure 16 across the width of the garment.

As used herein, the term "elastomeric" refers to a material or composite which can be elongated by at least 25 percent of its relaxed length and which will recover, upon release of the applied force, at least 10 percent of its elongation. It is generally preferred that the elastomeric strands be capable of being elongated by at least 100 percent, more preferably by at least 300 percent, of its relaxed length and recover, upon release of an applied force, at least 50 percent of its elongation.

Further, as used herein, the term "stretch bonded" refers to the situation wherein an elastomeric strand is bonded to the garment while said elastomeric strand is elongated at least about 25 percent of its relaxed length. Preferably, the term "stretch bonded" refers to the situation wherein the elastomeric strand is elongated at least about 100 percent, more preferably at least about 300 percent, of its relaxed length when it is bonded to the garment according to the present invention.

Finally, the term "bonded" refers to the joining, adhering, connecting, attaching, or the like of two materials to one another. As used herein, two elements will be considered to be bonded together when they are bonded directly one to another or indirectly such as when one of the elements is directly bonded to a third element which is in turn bonded to the other element.

As a general rule, it is desirable that the inner layer, outer layer and absorbent structure, and preferably all the elements of the garment be bonded together such that, when in a relaxed state, the elastomeric strands cause the inner layer, outer layer and absorbent structure, and preferably all of the elements of the garment to be reduced in length across the width of the garment. This reduction in length forms a plurality of rugosities in the garment generally perpendicular to the elastomeric strands. Since the inner layer, outer layer and absorbent structure are all reduced in length, it follows that they all contain a plurality of rugosities as a result of their reduced length. The garment is suitably reduced in length at least about 40 percent, preferably at least about 65 percent. That is, if the garment has a length of 50 inches in a stretched condition, in a relaxed condition its length is reduced at least about 40 percent (20 inches) thus making the garment about 30 inches in length.

It is particularly desired that the absorbent structure be reduced in length (gathered) by the elastomeric strands when the garment is in a relaxed state. Preferably, the absorbent structure is reduced in length across its entire width. By forming the garment such that the absorbent structure is reduced in length, more of the absorbent structure can be concentrated in the area where body fluids will be applied to the garment. Additionally, since the absorbent structure is capable of expanding longitudinally under an applied stretching force, the garment will adjust in length to fit a wide variety of users. Nonetheless, while the garment may be in a more extended state for certain users, the greatest possible amount of absorbent structure, for that user, will still generally be located in the area where it is most necessary. Because the garment is, in use, generally under an applied force and stretched to at least some degree, the presence of the elastomeric strands cause the garment, including the absorbent structure, to ride close against the body of a wearer. Thus, the garment is not as noticeable under clothing as known garments having an absorbent structure which does not contract along its length to adjust to the body of a wearer but instead, bunches and appears baggy when worn under clothes.

Figure 2:
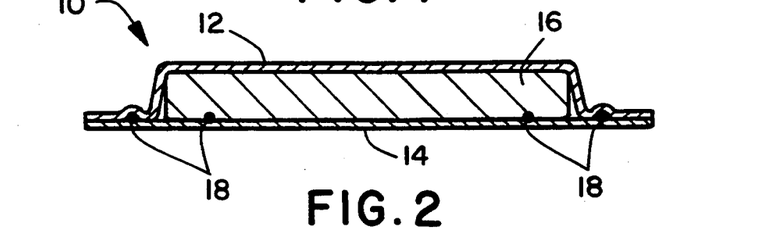
FIG. 2 is a cross section of FIG. 1 taken along line 2—2.

FIG. 2 is a cross section of the garment illustrated in FIG. 1 taken along line 2—2 of FIG. 1. As can be seen from reference to FIG. 2, absorbent structure 16 is located between the inner layer 12 and the outer layer 14. The outermost elastomeric strands 18 are stretch bonded to the inner layer 12 and the outer layer 14. The inner two elastomeric strands 18 are stretch bonded to the outer layer 14 and absorbent structure 16. In this manner, the inner layer 12, outer layer 14, and absorbent structure 16 will all be reduced in length along their width and form rugosities along their surface as the elastomeric strands are relaxed to a non-tensioned state.

Figure 3:
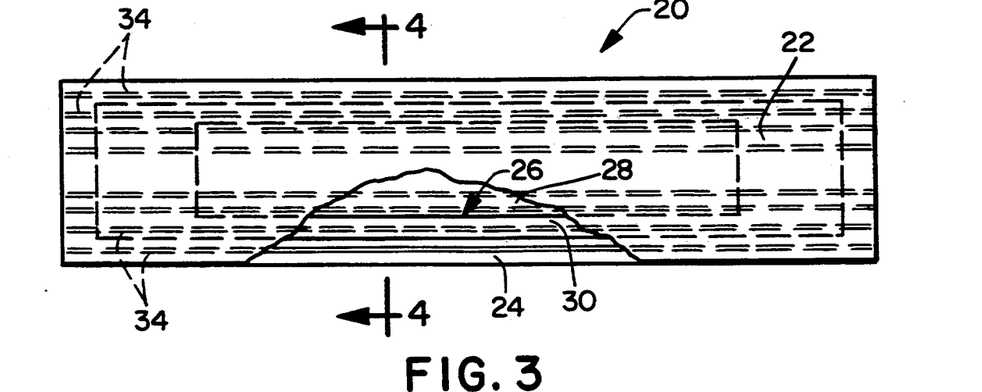
FIG. 3 is a top plan view of one embodiment of a stretchable absorbent garment according to the present invention in a stretched state.
Figure 4:
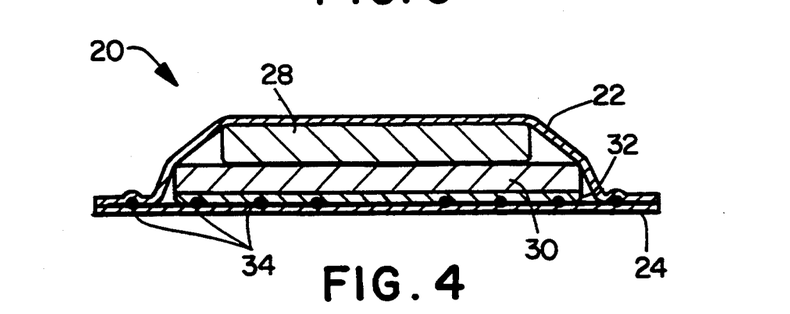
FIG. 4 is a cross section of the garment of FIG. 3 taken along line 4—4.

FIGS. 3 and 4 illustrate a second embodiment of the present invention. With reference to FIG. 3, a garment 20, is illustrated having an inner layer 22, an outer layer 24, and an absorbent structure 26 located between the inner layer 22 and the outer layer 24. In the embodiment of the present invention illustrated in FIGS. 3 and 4 the absorbent structure 26 comprises an upper layer 28, adapted to rapidly receive a discharged body fluid, a lower layer 30 adapted to primarily store a discharged body liquid and a fluid-impervious layer 32 adapted to prevent passage of a body fluid into lower layer 24 and externally of the garment 20.

Elastomeric strands 34 are stretch bonded along substantially the entire length of the garment. In the illustrated embodiment, the outermost elastomeric strands 34 are stretch bonded to the inner layer 22 and outer layer 24. The inner elastomeric strands are stretch bonded to the outer layer 24 and to the absorbent structure 26, specifically to the fluid-impervious layer 32 of absorbent structure 26. In order to ensure that all of the components of the garment 20 contract in length upon relaxation of the elastomeric strands 34, it is generally preferred that all of the elements be bonded to one another. Thus, it is preferred that the three elements of the absorbent structure 26 be bonded to one another and that the absorbent structure in turn be bonded to either or both of the outer layer 24 and inner layer 26. As is known to those skilled in the art, such bonding can be done with adhesives, heat, needling, ultrasonically, or the like. As will be described in greater detail below, the upper layer 28 and lower layer 30 of absorbent structure 26 are generally porous fiber matrixes. Due to the fibrous nature of the upper layer 28 and lower layer 30, said layers may be frictionally bonded to one another such that the interlocking of the fibers of the two components are sufficient to cause both components to contract in length when the garment is in the relaxed state.

Generally, it is desirable that the fluid-pervious inner layer be soft and have a generally clothlike feel, thus enhancing the comfort of a wearer. The inner layer may be a nonwoven web of synthetic or natural fibers or a blend thereof, a plastic film with perforations, an expanded plastic webbing material, a scrim material, or a woven material such as cotton or rayon. Preferably, the inner layer is spunbonded polyethylene or spunbonded polypropylene having a basis weight of about 0.2 to about 1.0 oz/yd$^2$. More preferably, the inner layer is spunbonded polypropylene having a basis weight of from about 0.2 to about 1.0 oz/yd$^2$. The material of which the inner layer will be made for any specific embodiment or variation can vary depending on the exact properties and characteristics desired of the inner layer. Generally, it is desired that the inner layer be hydrophobic and have high fluid transfer rates. When the inner layer is hydrophobic it tends not to hold fluid thus presenting a dryer surface for contacting the skin of a wearer. A high fluid transfer rate allows the inner layer to pass a discharged body fluid rapidly to prevent leakage from the garment. To achieve these characteristics, the inner layer can be treated with surfactants to adjust its hydrophobicity and fluid transfer rate and it may also be selectively embossed or apertured with discrete slits or holes extending therethrough to adjust its fluid transfer rate.

The absorbent structure is suitably any single or multilayered structure capable of absorbing discharged body fluids. Desirably, the absorbent structure is capable of absorbing a discharged body fluid at a rate generally equal to or greater than the rate at which said body fluid is discharged. Typically, the absorbent structure comprises at least one layer of an airlaid cellulosic fiber such as that commonly referred to as wood pulp fluff. Conventional airlaid cellulosic fiber layers can have a density ranging from about 0.05 to about 0.30 grams per cubic centimeter, measured under a load of 0.2 pounds per square inch, and are sufficiently flexible to readily conform to the body of a wearer. The absorbent structure may also comprise a coform material formed from a mixture of cellulosic fibers and synthetic polymer fibers. The coform material may be in replacement of or in addition to the layer of cellulosic fibers described above. For example, the coform material may comprise an airlaid blend of cellulosic fibers and meltblown polyolefin fibers, such as polyethylene and polypropylene fibers. It is generally preferred that the absorbent structure have at least one layer which has a tendency to draw a discharged body fluid away from the wearer and through and away from the inner layer such that the inner layer, in contact with the body of a wearer, tends to maintain a relatively dry feel.

The absorbent structure may also include an effective amount of an inorganic or organic high-absorbency material to enhance the absorptive capacity of the absorbent structure. For example, the absorbent structure can include 5 to 95 weight percent of high-absorbency material and preferably includes about 10 to 30 weight percent of the high-absorbency material to provide more efficient performance. Suitable inorganic high-absorbency materials include, for example, absorbent clays and silica gels. Organic high-absorbency materials can include natural materials such as agar, pectin, guar gum, and peat moss, as well as synthetic materials such as synthetic hydrogel polymers. Such hydrogel polymers include, for example, carboxymethylcellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Crosslinking may, for example, be by irradiation or by covalent, ionic, Van der Waals or hydrogen bonding. Suitable high-absorbency materials are available from various commercial vendors, such as Dow Chemical Company, Hoechst Celanese Corporation, Allied Colloid, and Stockhausen. Typically, the high-absorbency material is capable of absorbing at least about fifteen times its weight in a 0.9 weight percent aqueous solution of sodium chloride and preferably is capable of absorbing at least about 25 to 50 times its weight in a 0.9 weight percent aqueous solution of sodium chloride.

The high-absorbency material can be distributed or otherwise incorporated into the absorbent structure employing various techniques. For example, the high-absorbency material can be substantially uniformly distributed in a layer of airlaid cellulosic fibers or coform material when such layers are present in the absorbent structure. The material can also be non-uniformly distributed among the fibers to form, for example, a generally continuous gradient with either an increasing or decreasing concentration of high-absorbency material through the thickness of the absorbent structure. Alternatively, the high-absorbency material can comprise one or more discrete layers or strips selectively segregated from the other materials of the absorbent body. When the absorbent structure comprises a layer of airlaid cellulosic fibers, an optional hydrophilic tissue wrap may be present to help maintain the integrity of the airlaid fibrous structure. The tissue wrap typically comprises an absorbent cellulosic material such as creped wadding or a high wet-strength tissue.

In the embodiment of the present invention illustrated in FIGS. 3 and 4, the absorbent structure is a two-layer structure comprising an upper layer 28 and a lower layer 30. The upper layer 28 is designed to rapidly accept, temporarily hold, and subsequently release a body fluid. Specifically, it is desired that the upper layer be able to absorb discharged body fluids from the inner layer at the rate and volume said fluids are discharged. Then, it is desired that the upper layer be able to temporarily hold and subsequently release such absorbed fluid into the lower layer 30. After the upper layer has released the fluid into lower layer 30, upper layer 28 is ready to receive another insult of discharged body fluid. As a general rule, the upper layer will have a larger average pore size than the lower layer.

Exemplary of materials suitable for use as the upper layer 28 in a two-layer absorbent structure are needle entangled fibers (e.g., polyester fibers, rayon fibers, etc.), bonded fibers (e.g., polyester fibers, rayon fibers, etc.) and the like. Bonded polyester fibers suitable for use as the upper layer 28 are commercially available from Sackner Products, Grand Rapids, Mich. under the trade designation SH 66 Resinated Polyester Padding. The upper layer suitably has a thickness of from about 0.04 to about 1.0 inch, preferably from about 0.125 to about 0.75 inch, a density of from about 0.001 grams per cubic centimeter to about 1.0 grams per cubic centimeter.

The outer layer suitably comprises a soft, nonwoven material with a clothlike feel. Exemplary of suitable materials for use as the outer layer are spunbonded polypropylene, polyethylene, polyesters, and the like. Also suitable for use are meltblown polyolefins such as polyethylene, polypropylene and other meltblown thermoplastic materials such as polyesters. When spunbonded polypropylene or polyethylene are employed, the outer layer will generally be fluid-permeable.

In order to prevent a discharged body fluid from passing external of the garment, it is desirable to incorporate a fluid-impermeable layer into the garment. Exemplary of suitable fluid-impermeable layers are polyolefin films such as a film of polyethylene or polypropylene. It is possible to form the outer layer from a fluid-impermeable material thus obviating the necessity of incorporating a separate fluid-impermeable layer in the garment. However, softness of the garment is enhanced by having the outer layer comprise a nonwoven material with clothlike feel.

The elastomeric strands may be a single preferably threadlike length of elastomeric material or may be comprised of a plurality of threadlike lengths of elastomeric material. The strands generally have a transverse cross sectional area within the range of from about 0.005 to about 1.0 square millimeter, preferably from about 0.01 to about 0.6 square millimeter.

A variety of commercially available elastomeric materials can be used to form the elastomeric strands. Exemplary of suitable elastomeric materials from which the elastomeric strands may be formed are natural rubber, butyl rubber, or other synthetic rubber, urethane elastomeric material such as that available from B. F. Goodrich Company under the trademark TUFTANE, spun urethane elastomeric material such as spandex, and elastomeric material available from the H. B. Fuller Company under the tradename FULLASTIC. The latter material is based upon thermoplastic elastomeric copolymers of the A-B-A type such as those available from Shell Chemical under the trademark KRATON which have a rubbery midblock such as butadiene or isoprene and polystyrene end blocks and is especially useful because it is a self-adhesive material and can be applied to the garment without additional adhesive between the elastomeric strands and the other elements of the garment.

The generally parallel elastomeric strands, as illustrated in FIGS. 1 through 4, extend along substantially the entire length of the garment. In some instances, it may be desirable to have one or more elastomeric strands extend only along a partial length of the garment. This will be discussed in more detail below. For ease of manufacture, it is desirable that all of the elastomeric strands extend along the length of the garment and that there be no elastomeric strands in the transverse direction.

The various components of the garment are assembled together employing conventional techniques. For example, the components may be attached to one another employing thermal or sonic bonds, or mechanical fasteners such as snaps or clips. Alternatively, the components can be attached with adhesives, such as hot melt pressure-sensitive adhesives. The adhesives can be applied by employing conventional techniques such as by spraying droplets or filaments of adhesives. In the shown embodiments of the invention, the components are assembled employing an adhesive oriented along the length dimension of the garment.

The length of the outer and inner layers (prior to attachment of the elastomeric strands) will generally be within the range of from about 15 to about 80 inches, preferably from about 20 to about 65 inches. The width of the outer and inner layers will generally be within the range of from about 4 to about 8 inches, preferably from about 5 to about 7 inches. The length and width of the inner and outer layers may be the same or different. The length of the absorbent structure (prior to attachment of the elastomeric strands) will generally be within the range of from about 12 to about 25 inches, preferably from about 16 to about 20 inches. The width of the absorbent structure will generally be within the range of from about 2 to about 7 inches, preferably from about 3 to about 5 inches. As a general rule, the length and width of the absorbent structure will be less than the length and width of at least one of the outer or inner layers, preferably less than both the outer and inner layers.

In a relaxed state, the garment suitably has a length within the range of from about 5 to about 50 inches, preferably from about 7 to about 25 inches; and a width of from about 3 to about 8 inches, preferably from about 5 to about 6 inches.

Figure 5:
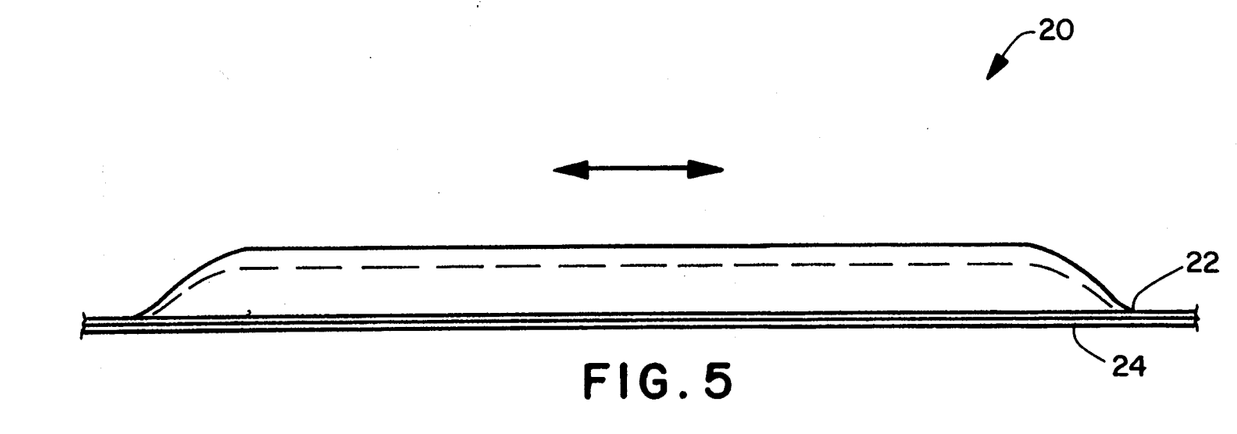
FIG. 5 is a side elevational view of the garment illustrated in FIG. 3 with the garment in a stretched state.
Figure 6:
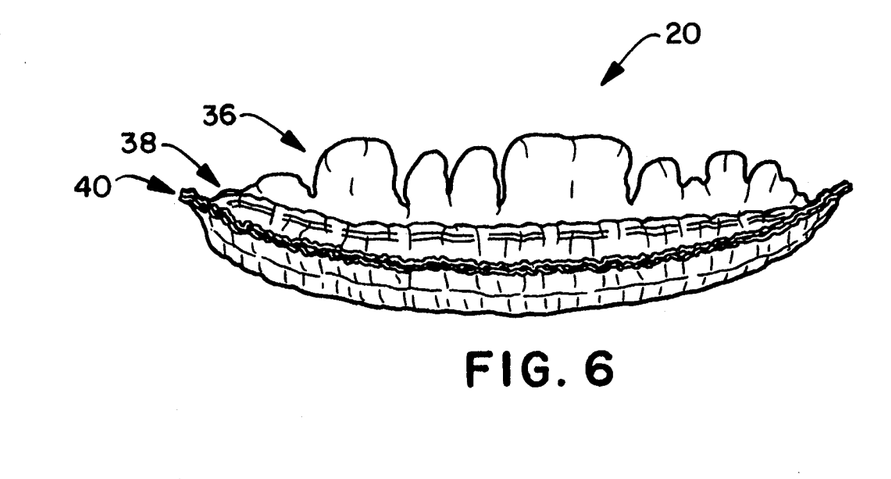
FIG. 6 is a side elevational view of the garment illustrated in FIG. 5 in a relaxed state.

Applicants have discovered a number of advantages which are achievable in the garments of the present invention. Referring now to FIGS. 5 and 6, FIG. 5 is a side elevational view of the longitudinal side of the garment illustrated in FIGS. 3 and 4 in an elongated tensioned state. FIG. 6 is a side elevational view of garment 20 in a relaxed state. Reference to FIG. 6 illustrates the extent to which the relaxed garment possesses a series of transverse rugosities. The area of garment 20 generally indicated by number 36 corresponds to the rugosities formed by allowing upper layer 28 of absorbent structure 26 to contract to a relaxed state. Due to the very open porous nature of upper layer 28, a billowy appearing set of rugosities is formed. The area of garment 20 generally represented by number 38 corresponds to lower layer 30 of absorbent structure 26 in a relaxed state. Due to the fact that, in the illustrated embodiment, lower layer 30 comprises an airlaid web of cellulosic fluff having a less porous nature than upper layer 28, lower layer 30 forms a less billowy appearing set of rugosities. The portion of garment 20 generally represented by the number 40 represents the rugosities formed in the area of the garment where the inner layer 22 is adhered directly to outer layer 24. Due to the thin, clothlike nature of inner layer 22 and outer layer 24, uniform appearing rugosities are formed. Due to the fact that the absorbent structure is less wide than the inner and outer layers and the elastomeric strand closest to the longitudinal edge of garment 20 is set back from the exact edge of the garment, the garment is found to possess, in a relaxed state, a ruffled appearance along its outer longitudinal edges. This ruffle contributes to the delicate appearance of the garment and increases the comfort to a wearer.

As can be seen from reference to FIG. 6, in a relaxed state, garment 20 possesses a longitudinal curve. The longitudinal curve of the garment is caused by the presence of the stretch bonded elastomeric strands. Specifically, the curve is caused by the fact that there is differential tensioning in the strands as a result of the location of the various strands in the garment. Specifically, assuming a constant tension on all the elastomeric strands, those strands at the outer longitudinal edges of the garment which are located between the inner layer 22 and the outer layer 24 exert a greater contractive force due to the fact that inner layer 22 and outer layer 24 are relatively easily gathered to form the rugosities. In contrast, those elastomeric strands located between the fluid-impervious layer 32 of the absorbent structure 26 and the outer layer 24, are able to contract to a lesser degree due to the fact that they must contract the absorbent structure 26 which is harder to gather due to its mass and thickness. Accordingly, due to the different degree of contraction between the inner elastomeric strands and the outer elastomeric strands, the longitudinal ends and edges of the garment tend to be pulled upwardly and inwardly, thus producing the illustrated curvature.

This differential tensioning may be induced, as described above, by the location of the elastomeric strands, or it may be induced or enhanced by differentially tensioning the strands prior to stretch bonding the strands to the garment. Alternatively, strands having different contractive forces can be employed to enhance this differential tensioning effect.

Applicants have discovered that in many instances it is desirable to impart a particular shape to the garments according to the present invention. The elastomeric strands present in the garments of the present invention can be positioned in different locations along the length and throughout the thickness of the garments. Accordingly, it is possible to achieve different garment shapes. The ability to shape the garment 20 can significantly increase the performance and comfort of the garment.

Figure 7:
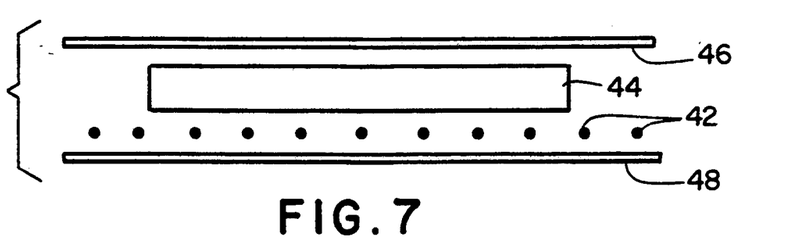
FIGS. 7 through 10 are exploded transverse end views of different preferred embodiments of garments according to the present invention.

Without intending to exhaust all possibilities, FIGS. 7 through 10 illustrate exploded transverse end views showing several possible locations of the various elements of garments according to the present invention. Referring to FIG. 7, the elastomeric strands 42 are located beneath an absorbent structure 44 which in turn is sandwiched between an inner layer 46 and an outer layer 48. As referenced in connection with FIG. 6, such a structure produces a garment having the outer longitudinal ends thereof curved upwardly and inwardly.

Figure 8:
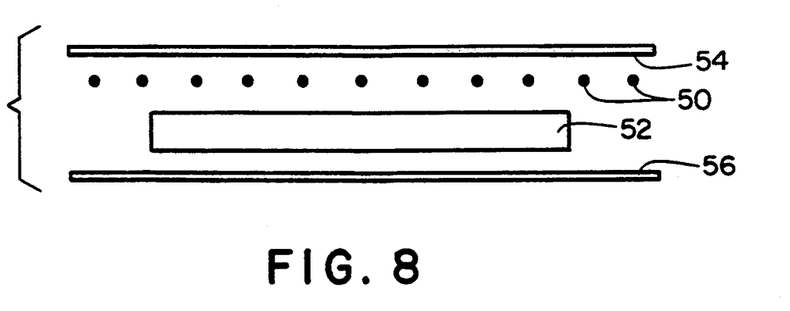

Referring to FIG. 8, elastomeric strands 50 are located above absorbent structure 52 which is in turn sandwiched between an inner layer 54 and an outer layer 56. Such an arrangement has been found to produce a garment wherein the longitudinal end of the garment tends to curve downward and inward, thus producing the mirror image curve of the garment of FIG. 7. Again, this shaping ability results from the specific location of the elastomeric strands.

Figure 9:
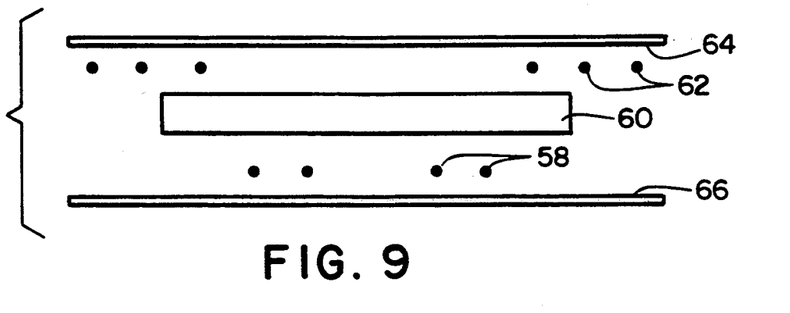

Referring to FIG. 9, two sets of elastomeric strands are present with the sets being located at different positions throughout the thickness of the garment. The elastomeric strands 58 are located beneath an absorbent structure 60 while elastomeric strands 62 are located above the absorbent structure 60. Strands 58 and 62 and absorbent structure 60 are sandwiched between an inner layer 64 and an outer layer 66. The arrangement illustrated in FIG. 9 has been found to produce a garment having the longitudinal ends of the garment curved upwardly and inwardly as with FIG. 7 but has further been found to produce a more pronounced upward and inward curve along the transverse edges of the garment. Thus, the arrangement illustrated in FIG. 9 has been found to produce a garment having a pocket configuration. Such a garment has been found to be particularly well adapted, from a performance and comfort standpoint, for use on humans.

It is believed that the location of the elastomeric strands throughout the thickness of the garment contributes to both the longitudinal and transverse curvature of the garment. One particularly advantageous aspect of the present invention is the ability to achieve transverse curvature of the garment without having elastomeric strands extend transversely across the width of the garment. Since the length of the garment often corresponds to the machine direction of the garment during formation, avoiding the necessity of having transverse (cross direction) elastomeric strands simplifies the manufacturing process.

Figure 10:
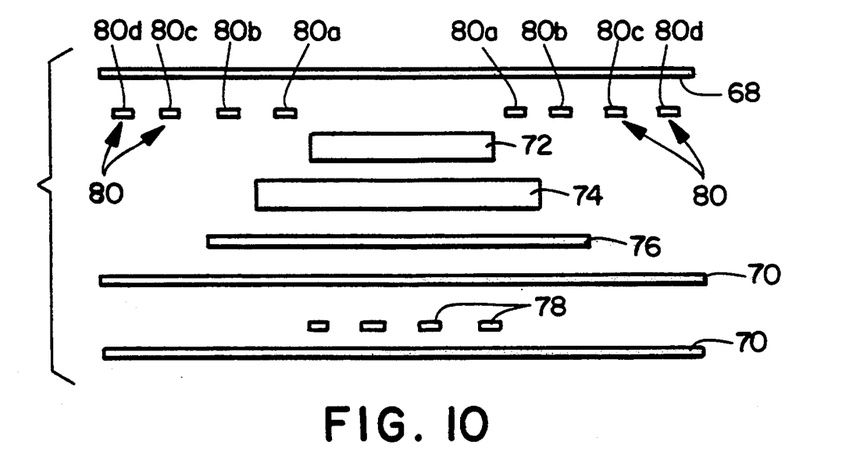

FIG. 10 illustrates yet another preferred embodiment of the present invention. In FIG. 10, inner layer 68 and a two component outer layer 70 enclose an absorbent structure comprising an upper layer 72, a lower layer 74, and a fluid-impervious layer 76. A first set of elastomeric strands 78 are located between the two components of outer layer 70. The elastomeric strands 78 are located in the central portion of the transverse cross section of the garment generally beneath the entire three layer absorbent structure. A second set of elastomeric strands 80 are located immediately beneath the inner layer 68. As can be seen from reference to FIG. 10, the inner two strands 80a of elastomeric strands 80 are located on the outer transverse edges of upper layer 72 and are sandwiched between lower layer 74 and inner layer 68. Elastomeric strands 80a may be full or only partial length strands. For example, the elastomeric strands 80a may extend generally only along the length of the absorbent structure. The elastomeric strands 80b are located on the outer transverse edges of lower layer 74 and are sandwiched between inner layer 68 and fluid-impervious layer 76. The remaining elastomeric strands 80c and 80d are located on the outer transverse edge of fluid-impervious layer 76 and are sandwiched between inner layer 68 and outer layer 70.

The particular arrangement of elements illustrated in FIG. 10 has been found to produce a garment having a particularly pronounced longitudinal and transverse curve. The presence of such curvature produces a garment which is improved from a performance and comfort standpoint.

Figure 11:
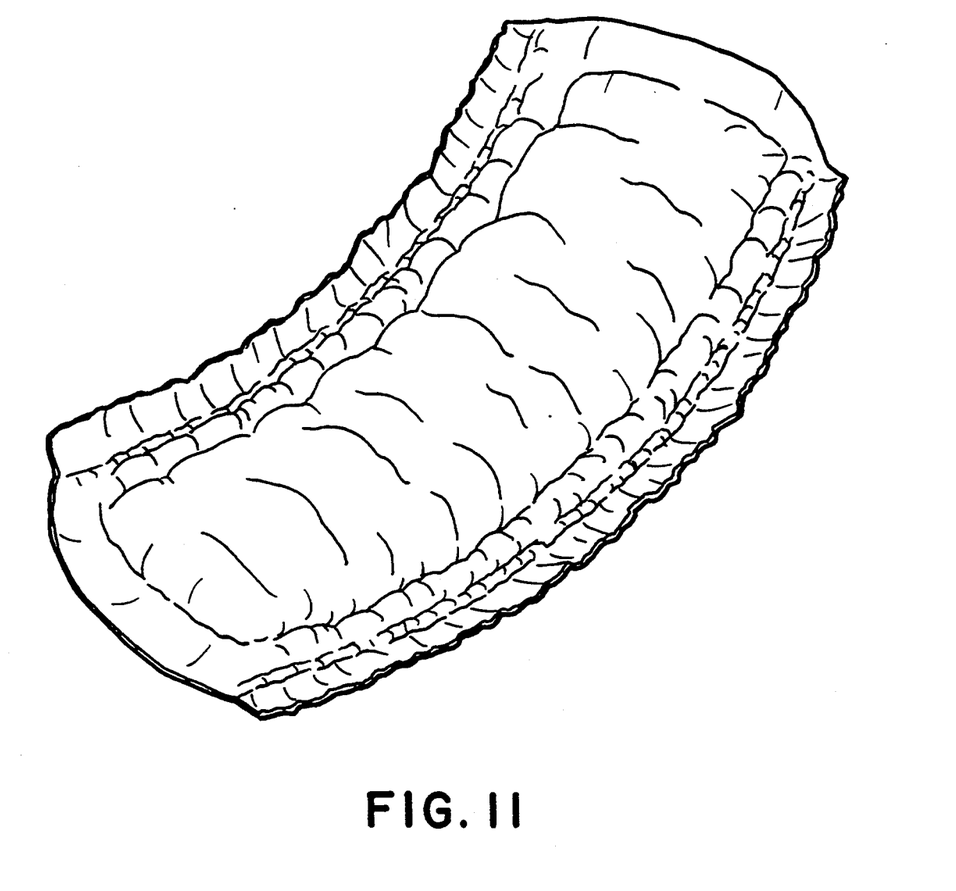
FIG. 11 is a perspective view of the garment illustrated in FIG. 10.

The garment illustrated in FIG. 11 is a perspective view of the embodiment illustrated in FIG. 10. As can be seen from reference to FIG. 11, the garment possesses a definite pocket shape. A garment such as that illustrated in FIG. 11 can be attached, in use, in a variety of manners. For example, an adhesive strip may be applied along the outer surface of the outer layer with the garment being held in position by attachment to the underclothing of a wearer. Alternatively, the adhesive material may be replaced with a frictious material which similarly holds the garment in position due to friction created between the garment and the underclothing of a wearer.

Figure 12:
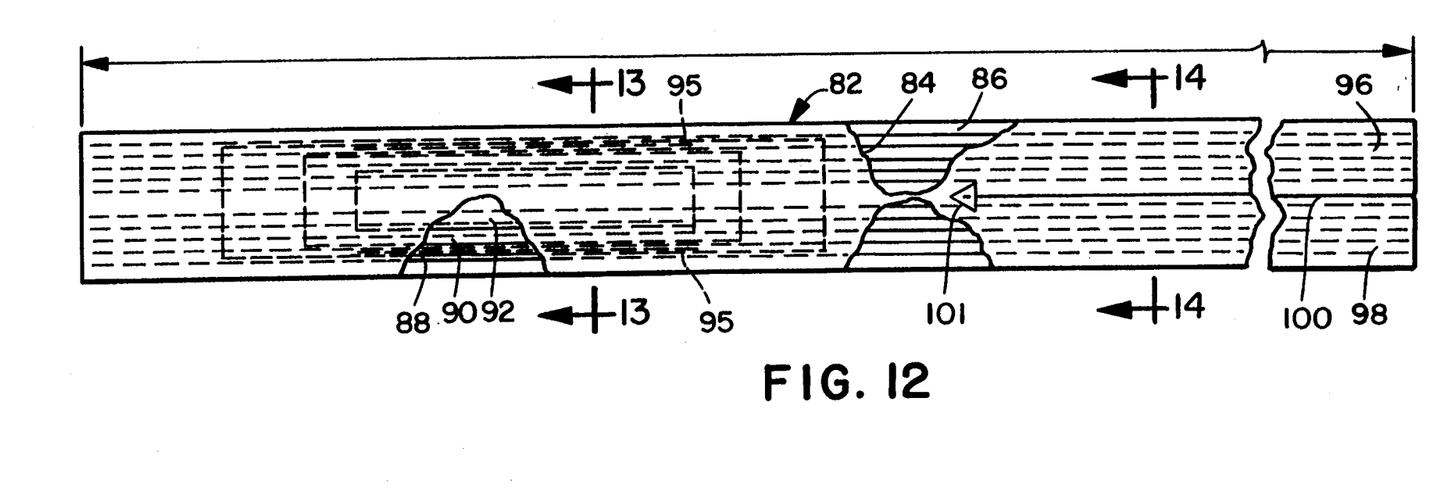
FIG. 12 is a top plan view of another embodiment according to the present invention illustrating the presence of attachment means integrally formed with the garment.

In another aspect, the present invention concerns a garment such as that described above further comprising integral attachment means. Such a garment is illustrated in FIG. 12. With reference to FIG. 12, a garment 82 is provided, said garment comprising an inner layer 84, an outer layer 86, and an absorbent structure comprising a fluid-impervious layer 88, a lower layer 90 and an upper layer 92. The garment further comprises a plurality of elastomeric strands 94 extending in a generally parallel relationship along the entire length of garment 82 and a pair of elastomeric strands 95 extending in a generally parallel relationship along only a partial length of garment 82. Again, the elastomeric strands 94 and 95 are stretch bonded to garment 82.

As can be seen from reference to FIG. 12, the absorbent structure is located generally at one longitudinal end section of garment 82. The other longitudinal end section comprises an extended area of inner layer 84 and outer layer 86 with stretch bonded elastomeric strands 94 sandwiched therebetween. Attachment means 96 and 98 are suitably formed by making a longitudinal slit 100 in the longitudinal end section of garment 82 generally opposite the absorbent structure. This produces two strips of a clothlike nonwoven material (inner layer 84 and outer layer 86) with at least one elastomeric strand stretch bonded to said nonwoven material. In a relaxed state, the attachment means 96 and 98 will constrict longitudinally thus forming a plurality of rugosities in their outer surface. By locating the elastomeric strands 94 slightly inward of the outer transverse edges of the attachment means 96 and 98, and forming slit 100 such that the elastomeric strands closest to slit 100 are set back slightly from slit 100 both the outer and inner edges of the attachment means 96 and 98 will have a ruffled appearance. The width of the longitudinal end section from which the attachment means is formed is desirably generally the same as the width of the longitudinal end of the garment on which the absorbent structure is located.

A reinforcing means 101 is present on garment 82. The reinforcing means 101 is located generally at one end of slit 100 and serves to prevent inadvertent lengthening of slit 100 during use of the garment. The reinforcing means 101 may comprise any material with sufficient strength to serve the above purpose and which is capable of being bonded to the garment. Exemplary of suitable material from which to form the reinforcing means are polymeric films such as polyethylene; woven and nonwoven fabrics, hot melt adhesives and the like.

Figure 13:
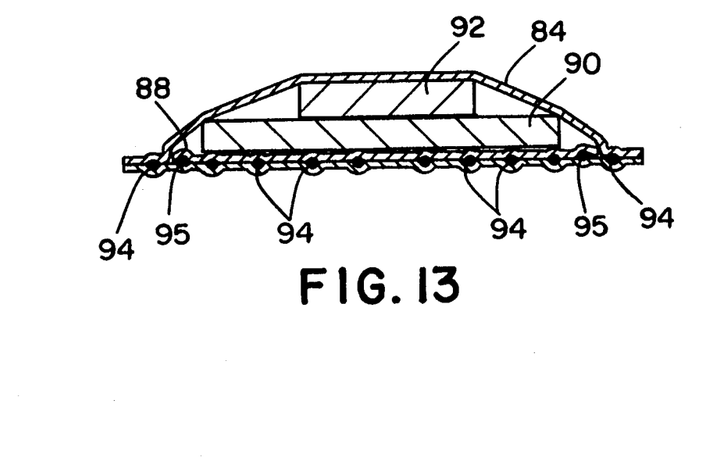
FIG. 13 is a cross section of the garment illustrated in FIG. 12 taken along line 13—13.
Figure 14:
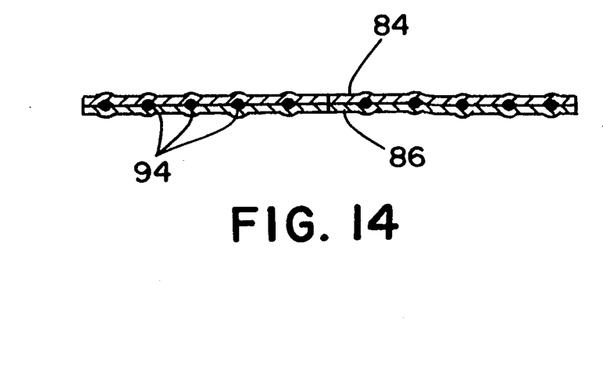
FIG. 14 is a cross section of the garment illustrated FIG. 12 taken a long line 14—14.

FIG. 13 is a cross-sectional view of FIG. 12 taken along line 13—13. FIG. 14 is a cross-sectional view of FIG. 12 taken along line 14—14.

Figure 15:
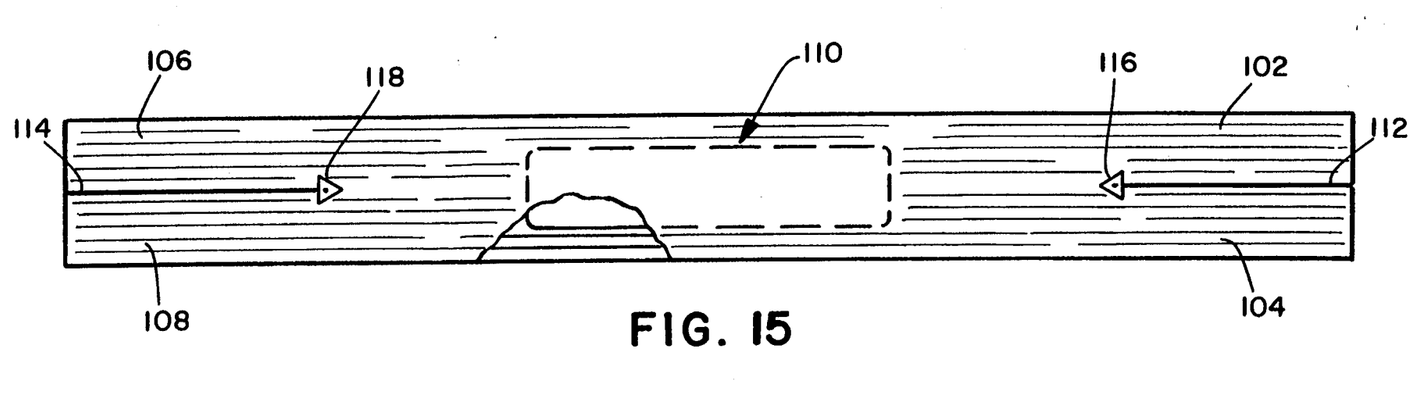
FIG. 15 is a top plan view of another embodiment according to the present invention indicating an alternative method of forming attachment means.
Figure 16:
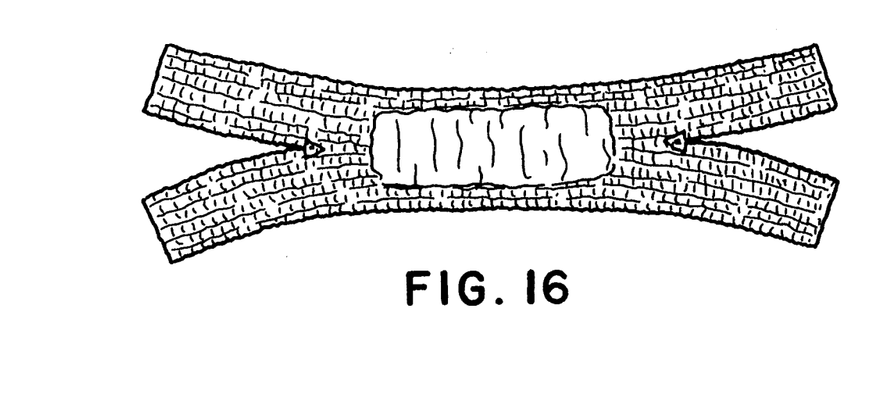
FIG. 16 illustrates the garment illustrated in FIG. 15 in a relaxed state.

FIG. 15 illustrates another preferred embodiment of the present invention further comprising attachment means. In the embodiment illustrated in FIG. 15, attachment means 102, 104, 106 and 108, similar to attachment means 96 and 98 of FIG. 12 are formed in both longitudinal ends of the garment with the absorbent structure 110 being located generally in the middle of the garment. Longitudinal slits 112 and 114 are formed at each longitudinal end of the garment to form the attachment means 102, 104, 106, and 108. Reinforcing means 116, 118 are illustrated at the ends of both of the slits which ends are closest to the absorbent structure. FIG. 16 illustrates a top plan view of the garment illustrated in FIG. 15 in a relaxed condition.

In use, the attachment means can be fitted with mechanical fasteners such as tapes, hook and loop type fasteners, buttons, hooks, and the like in order to fasten the garment about the hips and waist of a wearer.

Figure 17:
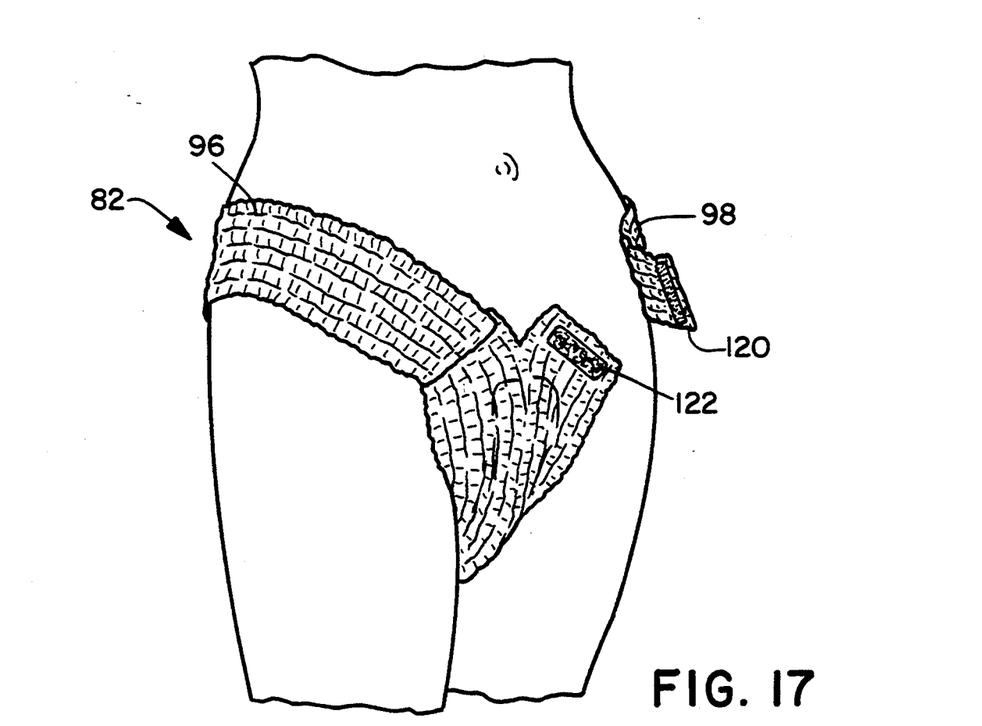
FIG. 17 is a front perspective view of the garment illustrated in FIG. 12 in use about the body of a wearer.
Figure 18:
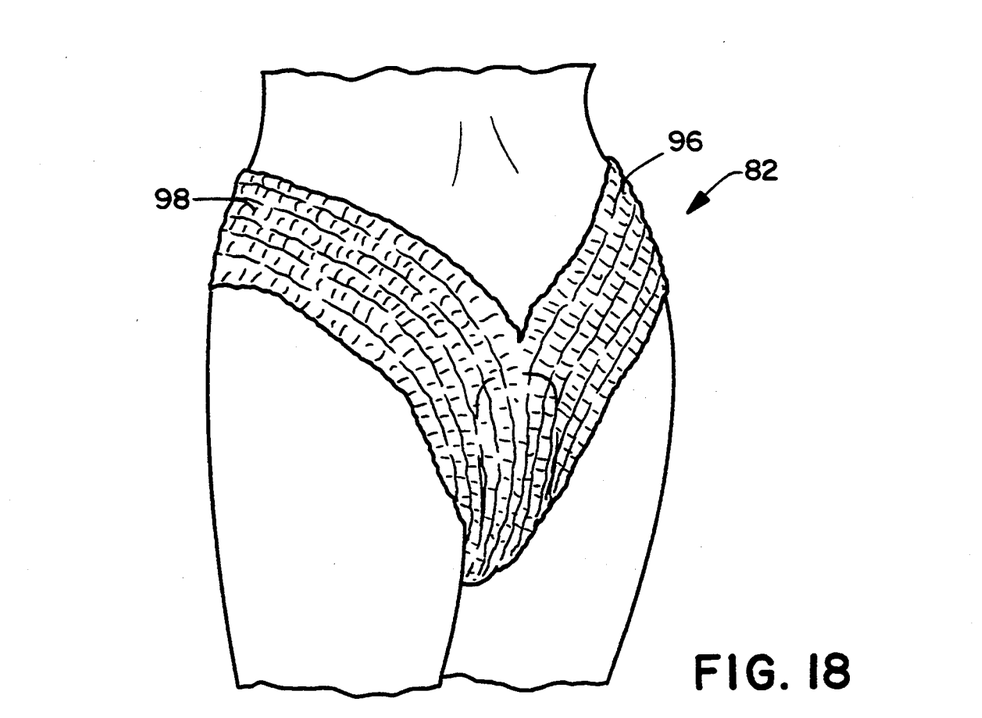
FIG. 18 is a rear perspective view of the garment illustrated in FIG. 12 in use about the body of a wearer.

FIGS. 17 and 18 illustrate the garment illustrated in FIG. 12 in use about the waist and hips of a wearer. Specifically, FIG. 17 is a front perspective view of the garment 82 in use on a wearer. As can be seen from reference to FIG. 17, attachment means 96 and 98 extend generally around the hips of a wearer and fasten to the opposite longitudinal end of garment 82. In the specific embodiment illustrated in FIGS. 17 and 18, a hook and loop type fastener have been attached to the garment. Specifically, a hook type fastener 120 has been attached to attachment means 98 with a loop type fastener 122 having been attached to the opposite longitudinal end of garment 82. FIG. 18 is a rear perspective view of the garment 82 being held in place by attachment means 96 and 98.

While not illustrated, it is evident that when the embodiment shown in FIGS. 15 and 16 is in place on a wearer the opposite ends of the garment will meet on the hips of the wearer. Thus, rather than the mechanical fasteners fastening together on the front of a wearer as illustrated in FIGS. 17 and 18, mechanical fasteners on the garment illustrated in FIGS. 15 and 16 would fasten together on the outside of a wearer's hips.

While the attachment means illustrated in FIGS. 12–18 have been shown to have been formed integrally with the garment, it is understood that the attachment means described above could be formed separately and integrally attached to a garment such as that illustrated in FIG. 11 to form a garment similar to that illustrated in FIGS. 12, 17 and 18. One advantage of forming the attachment means separately and attaching them to a garment as illustrated in FIG. 11 is that the elastomeric strands present in the attachment means could be varied in location, number, strength, and the like from that present in the portion of the garment containing the absorbent structure.

Figure 19:
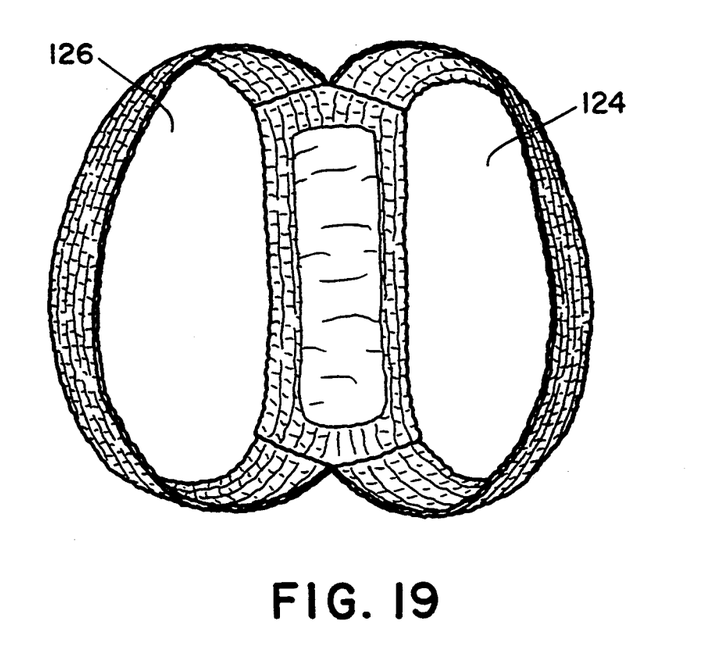
FIG. 19 is a perspective view of a stretchable absorbent garment according to one embodiment of the present invention.

Additionally, while the free end of the attachment means illustrated in FIGS. 12, 17 and 18 are shown to be capable of being releasably attached to the garment by mechanical fasteners, it is within the scope of the present invention to have the attachment means be permanently fixed to the garment at both ends. Such and embodiment is illustrated in FIG. 19. The garment illustrated in FIG. 19 would be applied to a wearer by having the wearer step through the openings 124, 126 and pulling the garment up over the wearer's legs until the garment is in proper position for use.

While this invention has been described as having a preferred embodiment, it shall be understood that it is capable of further modifications. Thus, this application is intended to cover any variations, uses or adaptations of the invention following the general principles thereof, and including such departures from the present disclosure as come within known or customary practice in the art to which this invention pertains and fall within the limits of the following claims.

What is claimed is:

1. A stretchable shaped absorbent garment having a length, a width, and a thickness, said garment comprising:
   (A) a fluid-pervious inner layer having a length and a width;
   (B) an outer layer having a length and a width;
   (C) an absorbent structure having a length and a width, said absorbent structure being located between said inner and outer layers; and
   (D) a plurality of generally parallel elastomeric strands stretch bonded to said garment along substantially its entire length, said elastomeric strands being located between said inner and outer layers, with at least one of said elastomeric strands being positioned between said inner layer and said absorbent structure and at least one of said elastomeric strands being positioned between said absorbent structure and said outer layer; such that, when in a relaxed state, said elastomeric strands reduce the length of said inner layer, outer layer, and absorbent structure across the width of the garment.

2. A garment according to claim 1 wherein said inner layer is a soft, clothlike, nonwoven material.

3. A garment according to claim 2 wherein said outer layer is a soft, clothlike, nonwoven material.

4. A garment according to claim 3 wherein the width of said absorbent structure is less than the width of at least one of said inner or outer layers.

5. A garment according to claim 4 wherein the width of said absorbent structure is less than the width of both of said inner and outer layers.

6. A garment according to claim 1 wherein, in a relaxed state, said elastomeric strands reduce the length of said inner layer, outer layer, and absorbent structure across the width of the garment by at least about 40 percent.

7. A garment according to claim 1 wherein said absorbent structure comprises a layer of cellulosic fibers and a high-absorbency material.

8. A garment according to claim 7 wherein said absorbent structure further comprises a layer which is capable of rapidly absorbing a liquid, temporarily holding said liquid and subsequently releasing said liquid.

9. A garment according to claim 1 wherein said garment further comprises a fluid-impervious layer located between said absorbent structure and said outer layer.

10. A garment according to claim 1 wherein said elastomeric stands are generally spaced across the entire width of said garment.

11. A garment according to claim 10 wherein the garment has a longitudinal curve.

12. A garment according to claim 11 wherein said garment has a transverse curve.

13. A garment according to claim 1 wherein at least one of said elastomeric strands is stretch bonded to said absorbent structure.

14. A garment according to claim 1 further comprising attachment means for holding said garment in place during used, said attachment means comprising at least two strips of a clothlike nonwoven material and at least one of said elastomeric strands stretch bonded to each of said strips of nonwoven material.

15. The garment according to claim 14 wherein said strips of nonwoven material have opposed longitudinal ends, one end being releasably attachable to said garment.

16. The garment according to claim 14 wherein said strips of nonwoven material have opposed longitudinal ends, both ends being integrally attached to said garment.

17. A garment according to claim 1 wherein at least one of said outer or inner layers defines an end section at one longitudinal end of said garment, said end section having a width and a length and having at least two generally parallel elastomeric strands stretch bonded along its length, said end section being slit along its length to form attachment means for holding said garment in place during use.

18. A garment according to claim 17 further comprising reinforcement means attached to said end section.

19. A garment according to claim 17 wherein said outer or inner layers define two end sections, one end section being located at each longitudinal end of said garment, said end sections having a width and a length and having at least two generally parallel elastomeric strands stretch bonded along their length, said end sections being slit along their length to form attachment means for holding said garment in place during use.

20. A garment according to claim 17 wherein the width of said end section is generally equal to the width of the garment.

21. A garment according to claim 1 where in a relaxed state, the elastomeric strands do not substantially reduce the width of the garment.

22. A stretchable shaped absorbent garment having a length, a width, and a thickness, said garment comprising:
- (A) a fluid-pervious inner layer having a length and a width;
- (B) an outer layer having a length and a width and being formed from a soft, clothlike, nonwoven material;
- (C) an absorbent structure having a length and a width, said absorbent structure comprising a layer of cellulosic fibers and a high-absorbency material and being located between said inner and outer layers;
- (D) a fluid-impervious layer located between said absorbent structure and said outer layer; and
- (E) at least four generally parallel elastomeric strands stretch bonded to said garment along substantially its entire length, with at least two of said elastomeric strands being located between said inner layer and said absorbent structure and at least two of said elastomeric strands being located between said absorbent structure and said outer layer; such that, when in a relaxed state, said elastomeric strands reduce the length of said inner layer, outer layer, absorbent structure, and fluid-impervious layer across the width of the garment by at least about 40 percent.

23. A method for forming a shaped absorbent garment said garment comprising a fluid-impervious inner layer having a length and a width, an outer layer having a length and a width, and an absorbent structure having a length and a width, said absorbent structure being located between said inner layer and said outer layer; the steps of the method comprising:
- (A) stretch bonding at least four generally parallel, elastomeric strands to said garment along substantially its entire length, at least two of said strands being positioned in different locations throughout the thickness of the garment, with at least one elastomeric strand positioned between said inner layer and said absorbent structure and at least one elastomeric strand positioned between said absorbent structure and said outer layer; and
- (B) bonding the inner layer, outer layer, and absorbent structure to one another.

24. The method according to claim 23 wherein the garment is void of transverse elastomeric strands.

* * * * *